United States Patent
Cotner et al.

(10) Patent No.: US 8,932,200 B2
(45) Date of Patent: Jan. 13, 2015

(54) DEVICE FOR THE TREATMENT OF URINARY INCONTINENCE

(76) Inventors: Ronald L. Cotner, Lakeland, FL (US); Steven Louis Lantagne, Salem, NH (US)

( * ) Notice: Subject to any disclaimer, the term of this patent is extended or adjusted under 35 U.S.C. 154(b) by 200 days.

(21) Appl. No.: 13/114,737

(22) Filed: May 24, 2011

(65) Prior Publication Data

US 2012/0130157 A1    May 24, 2012

Related U.S. Application Data

(60) Provisional application No. 61/347,584, filed on May 24, 2010.

(51) Int. Cl.
  *A61F 2/04*  (2013.01)
  *A61F 2/00*  (2006.01)
(52) U.S. Cl.
  CPC .................................. *A61F 2/0036* (2013.01)
  USPC ........................................................... 600/31
(58) Field of Classification Search
  USPC ................... 600/30–32, 37; 606/151, 157; 623/23.64–23.66; 128/885; 607/40–41
  See application file for complete search history.

(56) References Cited

U.S. PATENT DOCUMENTS

| | | | |
|---|---|---|---|
| 3,640,282 A | 2/1972 | Kamen et al. | |
| 4,019,499 A | 4/1977 | Fitzgerald | |
| 4,167,952 A | 9/1979 | Reinicke | |
| 4,417,567 A * | 11/1983 | Trick | 600/31 |
| 4,556,050 A | 12/1985 | Hodgson et al. | |
| 4,584,990 A * | 4/1986 | Haber et al. | 600/31 |
| 4,587,954 A | 5/1986 | Haber | |
| 4,994,020 A * | 2/1991 | Polyak | 600/31 |
| 5,007,894 A * | 4/1991 | Enhorning | 600/29 |
| 5,088,980 A | 2/1992 | Leighton | |
| 5,480,434 A * | 1/1996 | Eckstein et al. | 128/898 |
| 5,509,888 A * | 4/1996 | Miller | 600/29 |
| 5,782,916 A | 7/1998 | Pintauro et al. | |
| 5,888,188 A | 3/1999 | Srougi et al. | |
| 5,893,826 A | 4/1999 | Salama | |
| 6,491,623 B2 * | 12/2002 | Snyder et al. | 600/31 |
| 7,470,228 B2 | 12/2008 | Connors et al. | |
| 7,530,943 B2 * | 5/2009 | Lechner | 600/37 |
| 2002/0111530 A1 | 8/2002 | Bakane | |
| 2003/0144575 A1 | 7/2003 | Forsell | |
| 2003/0144648 A1 | 7/2003 | Forsell | |

(Continued)

OTHER PUBLICATIONS

See International Search Report corresponding to International Application No. PCT/US2012/031967.

(Continued)

*Primary Examiner* — Christine Matthews
*Assistant Examiner* — Joshua D Lannu
(74) *Attorney, Agent, or Firm* — Davis & Bujold, PLLC; Michael J. Bujold

(57) ABSTRACT

A device for treating urinary incontinence. The device comprising a body having a passage, for accommodating a urethra of a patient, extending from an inlet to an outlet of the device. The passage being configured so as to normally induce a flow obstruction in the urethra, following surgical implantation of the device. The flow obstruction, induced by the device, being sufficiently pliable and deformable so that once an internal system pressure within the urethra becomes sufficiently great, the internal system pressure overcomes the flow obstruction, induced by the device, and creates a flow passage through the device.

17 Claims, 8 Drawing Sheets

(56) References Cited

U.S. PATENT DOCUMENTS

2006/0167337 A1    7/2006   Forsell
2008/0045783 A1*   2/2008   Forsell .......................... 600/30
2010/0160716 A1*   6/2010   Snow ............................ 600/31

OTHER PUBLICATIONS

Written Opinion of the International Searching Authority corresponding to Application No. PCT/US2012/031967.

* cited by examiner

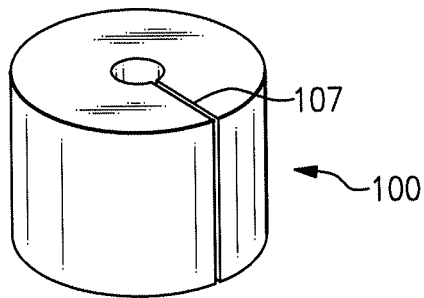
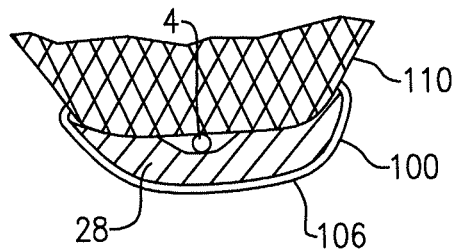
FIG.12A    FIG.12B
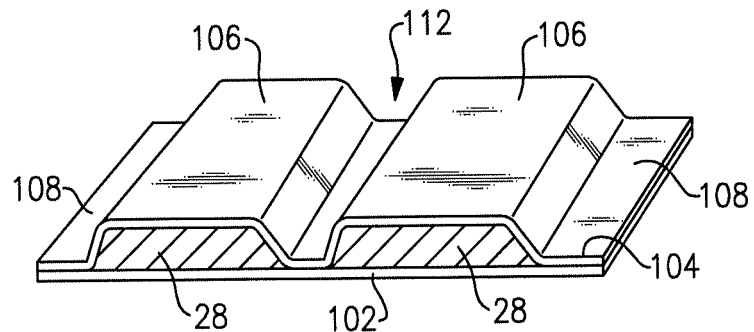
FIG.13
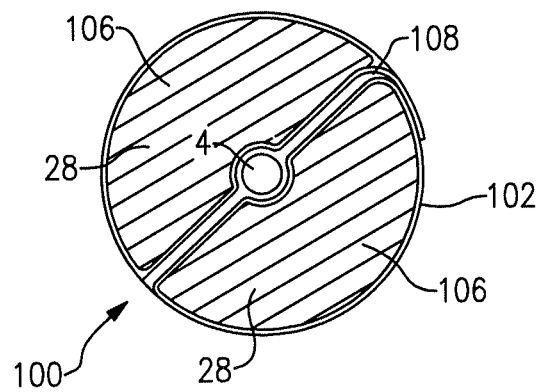
FIG.14

DEVICE FOR THE TREATMENT OF URINARY INCONTINENCE

This application claims priority from U.S. Provisional Patent Application No. 61/347,584 filed May 24, 2010.

FIELD OF THE INVENTION

The present invention generally relates to a device for the treatment of urinary incontinence as well as a variety of other anatomical and physiological processes and/or systems of the human body.

BACKGROUND OF THE INVENTION

Urinary incontinence is a condition found in both males and females and manifests itself such that the bladder, the associated sphincter muscles, prostate gland and/or the urethra malfunctions allowing urine to leak due to the compromise of normal anatomical/physiologic control. Often, urinary incontinence results in the soiling of the person's garments causing emotional, psychological and social issues. As stated, this problem/condition can affect both men and woman; usually exhibited later in life as the urinary tract (system) either weakens or otherwise ceases to properly function due to the natural aging process, stress related to obesity, physical damage or damage due to disease of the urinary system or any of its components and surrounding anatomical structures (prostate, bladder, urethra, musculature, etc.) or secondary to the treatment of diseases such as cancer in and around the area of the urinary system. It is also seen in postpartum or postmenopausal woman that have experienced changes in their uterus, bladder and/or other parts of the urinary system. It is to be appreciated that obesity and "stress incontinence" are often related.

SUMMARY OF THE INVENTION

The device for the treatment of urinary incontinence is a surgically implanted device and is designed to rest against or to circumvent the urethra and/or prostate or some other related anatomical structure(s). The device functions by causing an obstruction to the urethra, i.e., the "urethra non-patent state," so as to interrupt the flow of urine through the urethra or some other related anatomical structure(s). The obstruction can be induced by the application of a constrictive force, a restrictive impediment or sufficient external pressure or force, on or around the urethra so as to collapse and sufficiently close the urethra and/or other structures and thereby maintain the urethra in a non-patent state. That is, the device is shaped, in its normal state, to reconfigure the urethra into the "urethra non-patent state" and thereby overcome the internal system pressure in the urinary tract such that the urethra collapses, constricts, bends or is otherwise reconfigured so that the urine is reliably and consistently prevented from flowing from the bladder through the urethra for discharge from the individual. In addition, such "urethra non-patent state" which collapses, constricts, bends or is otherwise reconfigures the urethra and reliably and consistently prevents the flow of urine, must not be sufficiently great so as to cause any trauma or other permanent harm or damage to the urethra.

When the internal system pressure within the bladder and the urinary tract of the patient increases, a sensory message is transmitted to the brain of the individual that micturition is necessary. A normal systemic function proceeds with the bladder muscles and the abdominal muscles contracting and the bladder sphincter muscle relaxing. This normal systemic function creates an internal system pressure that is sufficiently high enough to overcome the "urethra non-patent state" induced by the device, so that the urethra correspondingly commences to open and thereby permits the flow of urine through the urethra from the bladder, through the device, and out of the body in a normal fashion. The device thus allows for normal urethra patency as the device is forced, by the internal system pressure into the "urethra patent state."

As soon as the internal system pressure of urine in the bladder and flowing along the urinary tract falls below the threshold of the "urethra patent state," the device begins to overcome the internal system pressure caused by the urine flow and naturally and inherently returns back to its "urethra non-patent state" so that the flow of urine subsides and discontinues. That is, the device returns back to its normal state which, in turn, causes the urethra to return back to its non-patent state thereby preventing the flow of urine and an end to the micturition process. This process is inherent to the gradual change in the internal system pressure provided by the anatomical and physiological changes during the micturition process and the mechanical and design parameters of the device whereas the patent and non-patent states are maintained.

It is to be appreciated that there are a variety of different shapes and/or configurations of the device that will allow the device to function in the above manner, i.e., induce a "urethra non-patent state" or "flow obstruction" which will be reconfigurable into a "urethra patent state" or "flow passage" upon experiencing a "sufficient internal system pressure." There may also be features external to a main body of the device which achieve or enhance the efficacy of the device. Examples of such shape configurations and other features will be discussed below as part of the device design.

The device may also be used to support, the bladder and other related anatomical structures following the removal of the prostate and the surgical implantation of the device.

The device for treating urinary incontinence according to the invention comprises a body with a laterally outer surface, an inlet end surface, a outlet end surface and an inner surface which defines a passage that extends through the device from the inlet end surface to the outlet end surface. The inlet and outlet surfaces being integral with axially opposite ends of each of the inner and outer surfaces to define an interior of the device. The interior of the device being filled with a medium. The inner surface being movable with respect to the outer surface between a first position and a second position depending on a difference between the desired pressure or force from within the interior of the device and a internal system pressure in the urinary tract such that a diameter of the passage, when the inner surface is in the first position, is smaller than a diameter of the passage when the inner surface is in the second position.

The device may also be used to support the bladder sphincter of a paraplegic who normally uses a catheter to periodically empty the bladder instead of using one which is permanently attached.

As used within this patent application and the appended claims, the term "flow obstruction" is intended to mean that the flow of urine through the urethra is temporarily obstructed, blocked and/or otherwise discontinued due to the device overcoming a sufficiently low internal system pressure in the urinary tract, as a result of relaxed bladder and abdominal muscles and a contracted bladder sphincter muscle, such that the device collapses, constricts, bends, folds or otherwise reconfigures the urethra so that the urine is reliably and consistently prevented from flowing from the bladder and through the urethra.

As use within this patent application and the appended claims, the term "flow passage" is intended to mean that the flow of urine through the urethra is temporarily permitted due to the internal system pressure in the urinary tract becoming sufficiently great, as a result of contraction of the bladder and abdominal muscles and a relaxation of bladder sphincter muscle, such that the urethra overcomes the flow obstruction, e.g., the collapse, constriction, bend, fold or other reconfiguration of the urethra, induced, caused or otherwise created by the device so that the urine can thus reliably and consistently flow from the bladder and through the urethra and, once the internal system pressure in the urinary tract sufficiently decreases, the device is allowed to return to its normal state and induce the "flow obstruction" in the urethra.

As used within this patent application and the appended claims, the term "internal system pressure" is intended to mean the pressure of the urine located within the urinary tract, between the bladder and the device, which is attempting to counteract the flow obstruction induced, caused or otherwise created in the urethra by the device.

BRIEF DESCRIPTION OF THE DRAWINGS

The invention will now be described, by way of example, with reference to the accompanying drawings in which:

FIG. 12A is a diagrammatic perspective view of the device according to FIG. 12 wrapped in a cylindrical configuration;

FIG. 12B is a diagrammatic cross sectional view of the device according to FIG. 11 that is implanted to press the urethra against an anatomical feature of a patient;

FIG. 13 is a diagrammatic cross sectional perspective view of another embodiment of the device according to the invention having a planar configuration and multiple shells;

FIG. 14 is a diagrammatic cross sectional view of the device according to FIG. 13 wrapped around the urethra of a patient;

DETAILED DESCRIPTION OF THE INVENTION

Figure 1:
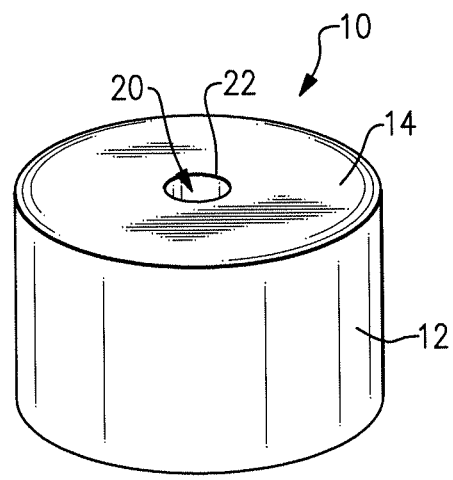
FIG. 1 is a diagrammatic perspective view of an embodiment of the device for the treatment of urinary incontinence, according to the invention, having a single shell.

It is to be appreciated that the device 10 may have a variety of different design configurations, shapes and sizes so as to meet the physiological functional needs/requirements of either male or female patients. Although the device 10 can be utilized in relation to a number of different physiological processes and/or systems, the device 10 will be generally described below in relation to the treatment of urinary incontinence. In this case, the physical shape of the device 10 may take on a variety of configurations, shapes and sizes so as to facilitate normal physiological urinary function and the eliminate urinary leak or incontinence. For this purpose, ideally for the male that has had his prostate gland removed (prostatectomy) or the normal functioning of the bladder, sphincter muscles, urethra and/or prostate gland has been lost due to radiation therapy or any other cause of tissue damage, the device 10 can be formed so as to have the shape of the normal prostate gland. This configuration allows for normal bodily function as well as provide support for the bladder that was normally previously provided by the prostate gland, prior to removal thereof due to disease, damage, etc. In this case, the device 10 can also have the shape of a barrel, a marshmallow or a walnut or some other similar or desired shape so as to provide the desired functional results.

The device 10, for the treatment of urinary incontinence, will now be generally described with reference to FIGS. 1 and 2A-2D. As seen in those figures, the urethra 2 extends downward vertically from the bladder 4 and the bladder sphincter muscle 6 and enters and passes through the device 10. The device 10 is vertically aligned and comprises a circumferential outer wall or surface 12 and opposed inlet and outlet end surfaces 14, 16. The device 10 also has a passage 20 that extends completely through the device 10, from the inlet end surface 14 to and the outlet end surface 16. A radially inner surface 18 of the device 10 defines the passage 20. The urethra 2 is normally accommodated within the passage 20 as the urethra 2 spans or extends through and is surrounded by the device 10. The device 10 facilitates reconfiguration of the urethra into the "urethra non-patent state", i.e., creates the flow obstruction, and thereby overcome the internal system pressure within the urinary tract such that the urethra collapses, constricts, bends, folds or otherwise reconfigured so that the urine is reliably and consistently prevented from flowing from the bladder through the urethra.

As mentioned above, the shape and dimensions of the device 10 depend somewhat on the physiological functional need/requirement of the patient. In relation to the treatment of urinary incontinence, the device 10 is shaped and dimensioned such that a height of the device 10, i.e., the vertical distance from the inlet surface 14 to the outlet surface 16, is generally preferably in the range of between 0.2 to 5.0 inches, or more preferably between about 0.4 to 3.5 inches. As shown in FIG. 1, the device 10 is substantially cylindrical with a width of the device 10, i.e., the horizontal distance between opposite lateral sides of the device 10, generally referred to as an outer diameter of the device. The outer diameter of the device 10 is preferably in the range of between about 0.5 to 7.0 inches, or more preferably between about 1.0 to 5.0 inches.

The matriculation process of a patient with the device 10 surgically implanted will now be described with reference to FIGS. 2A-2D. As shown in those figures, the urethra 2 enters via a first inlet end surface 14 of the device 10, via an inlet 22 and extends along the passage 20 through the device 10 and eventually exits through the outlet 24 formed in the outlet end surface 16.

Figure 2A:
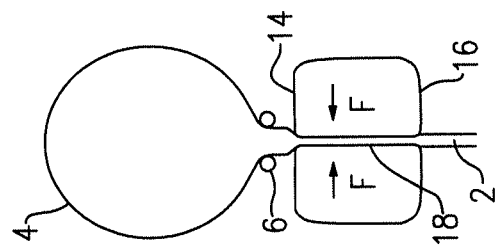
FIGS. 2A, 2B, 2C and 2D are diagrammatic cross sectional views of the device of FIG. 1 shown in different positions during the matriculation process.

The inner wall or surface 18 of the device 10, which defines the passage 20 through which the urethra 2 passes, is normally compliant, pliable or ductile such that the inner wall or surface 18 can respond to different forces and/or pressures placed thereon to facilitate either permitting flow through the urethra 2 or create or induce, cause or induce a sufficient collapse, constriction, bend or other reconfiguration of the urethra, i.e., the flow obstruction, so that the urine is reliably and consistently prevented from flowing from the bladder through the urethra, i.e., the urethra non-patent state. There are generally two opposing pressures or forces that can be applied on and/or by the inner wall or surface 18 of the device 10. In the normal state of the device, as seen in FIGS. 2A and 2D, an external obstruction pressure or force F (such as a constrictive force, a collapse force, bending force, a folding force or some other reconfiguration force) is applied on and/or by the inner wall or surface 18, generally in a radially inward direction as indicated in the figures, by at least one of a number of different means, so as to sufficiently reduce the internal dimensions of the passage 20, i.e., create, cause or induce the flow obstruction, and thereby prevent flow through the urethra 2. That is, in the normal state of the device 10, the inner wall or surface 18 is influenced to apply the obstruction pressure or force F radially inward toward and against the urethra 2 so that the diameter of the passage 20 is reduce to a minimum and flow therethrough is prevented. In the urethra non-patent state generally shown in FIGS. 2A and 2D, the inner wall or surface 18 generally collapses the urethra 2 and obstructs flow through the urethra 2 thus preventing the passage of urine U therethrough, i.e., creates the flow obstruction.

Over the course of normal systemic function, the bladder eventually fills with the urine U. When the bladder becomes sufficiently full with the urine U, the abdominal muscles contract and the bladder sphincter muscle 6 correspondingly relaxes, and an internal system pressure (positive pressure) is produced within the bladder 4. The internal system pressure acts upon the urethra 2 and the urethra 2, in turn, counteracts and overcomes the obstruction pressure or force applied thereto by the inner wall or surface 18 of the device 10. Once the internal system pressure of the urine U, contained within the bladder 4 and applied to the internal flow passage of the urethra 2, is greater than the obstruction pressure or force F applied by the inner wall or surface 18 of the device 10, the inner wall or surface 18 of the device 10 is biased sufficiently radially outward so that the urethra 2 becomes patent thereafter, i.e., achieves a "urethra patent state" with a flow passage, and the urine U is thereafter free to flow along the urethra 2 from the bladder 4 through the device 10 and out of the body in a normal fashion.

Figure 2B:
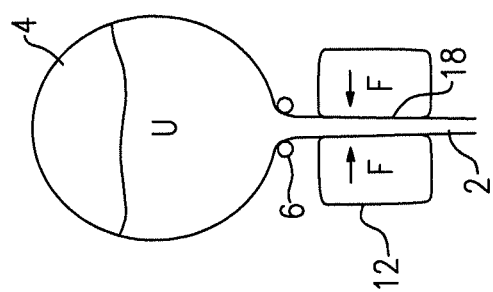
Figure 2C:
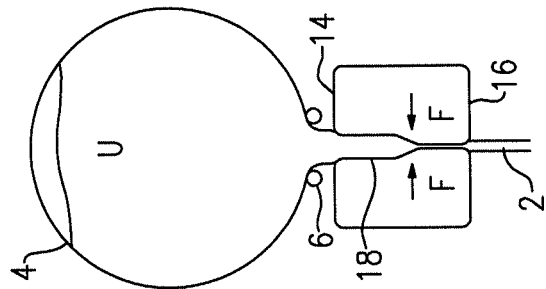
Figure 2D:
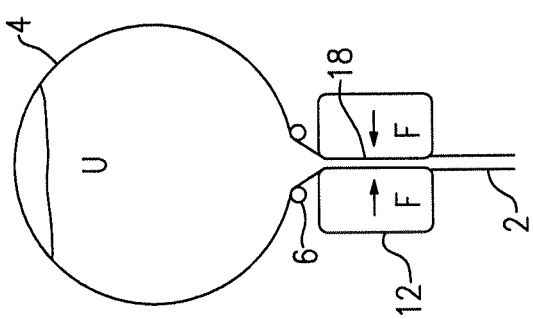

FIG. 2B diagrammatically shows the passage 20 being transformed, by the internal system pressure of the urethra 2, from the urethra fully non-patent state in which the urine U is prevented from flowing from the bladder 4 through the urethra 2 and out of the individual, into the urethra fully patent state, i.e., the passage 20 through the device is being transformed by the internal system pressure to create or cause a flow passage through the urethra 2. FIG. 2C diagrammatically shows the urethra 2 in its fully patent state in which the passage 20 was sufficiently biased radially outwardly, by the internal system pressure of the urethra 2, so that the urine U is relatively free to flow from the bladder 4 through the urethra 2 and out of the individual.

Once the bladder 4 has been sufficiently emptied (FIG. 2D), the bladder muscles and the abdominal muscles again began to relax and the bladder sphincter muscle 6 again began to constrict which, in turn, reduces the internal system pressure of the urine U flowing along and within the urethra 2. As soon as the obstruction pressure or force F applied by the inner wall or surface 18, against the urethra 2, becomes greater than the internal system pressure applied by the urine U contained within the urethra 2, the inner wall or surface 18 again gradually transforms back into its normal and inherent configuration or state in which the inner wall or surface 18 again induces, creates or otherwise causes the flow obstruction, e.g., the inner wall or surface 18 constricts, collapses, bends or other reconfigures the urethra 2 and thereby prevents the further passage of urine U therethrough so that the urethra 2 returns back to its non-patent state.

To facilitate the desired flow and interruption in flow through the urethra 2, the passage 20 generally needs to be sized, e.g., have a diameter so as to readily accommodate and receive the urethra 2 therein and maintain the urethra 2 in a constricted, collapsed, bent, folding or some other reconfigured state when the device 10 is in a normal inherent state while also be able to be sufficiently deformed once the internal system pressure of urine flowing within the urethra 2 overcomes the constrictive, collapsing, bending, folding or some other reconfiguration force of the device 10. It is preferable that the passage 20, in its normal state, has a passage diameter between 0.04 to 2.3 inches, or more preferably a diameter of between about 0.05 to 2.0 inches.

Figure 3:
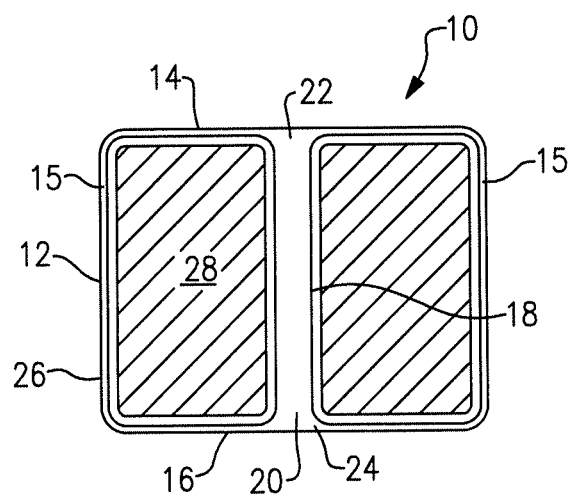
FIG. 3 is a diagrammatic cross sectional view of an embodiment of the device according to the invention having a single shell.

As shown in FIG. 3, the device 10 comprises an exterior sac, pouch or shell 26 which has thin walls that are at least somewhat elastomeric. The sac, pouch or shell 26 can encase a preformed foam body or is sufficiently filled with a foam, a gel, a liquid, a gas or some other generally viscous medium 28. Since the device 10 is to be implanted in the body of a patient, all the materials utilized either for manufacture of or implementation into the device 10 must be bio-compatible. The sac, pouch or shell 26 can be formed from one or more bio-compatible materials such as a radiopaque material, for example. Similarly, the preformed foam body or the foam, gel, liquid, gas or other viscous medium 28 can comprise one or more bio-compatible materials. In one version of this embodiment the sac, pouch or shell 26 surrounds a preformed body which can be made with a bio-compatible foam. The sac, pouch or shell 26 and thus the device 10, in this case, assumes the shape, size and/or configuration of the preformed body which can be formed in a manner discussed below. In another version of this embodiment the sac, pouch or shell 26 is filled with enough foam, gel, liquid, gas and/or other viscous medium 28 such that the device 10 normally assumes the desired shape, size and/or configuration which in this case is at least partly dependant on the constraints of the sac, pouch or shell 26. It is to be appreciated that by adjusting the volume of the foam, the gel, the liquid, the gas and/or the other viscous medium 28 contained within the internal chamber of the device 10, the relative spacing of the opposes inner walls 18 from one another, i.e., the internal diameter of the passage 20, can be correspondingly adjusted, and thus the cross-sectional size of the passage 20 can be customized and fit the specific needs of the individual patient. For example, in the version of the device 10 in which the preformed body is encased within a sac, pouch or shell 26, it is to be appreciated that the constrictive, collapsing, bending, folding or some other reconfiguring force or pressure may be adjusted by injecting a foam, gel, liquid, gas and/or other viscous medium into the sac, pouch or shell 26. In the version of the device 10 in which the sac, pouch or shell 26 is filled with foam, gel, liquid, gas and/or other viscous medium 28, an additional amount of foam, gel, liquid, gas and/or other viscous medium 28 may be introduced into the device 10 to reduce the cross-sectional diameter of the passage 20 and correspondingly increase the constrictive, collapsing, bending, folding or some other reconfiguring force or pressure applied by the device 10 to the exterior surface of the urethra 2. Alternatively, less foam, gel, liquid, gas and/or other viscous medium 28 may be introduced into the device 10 to increase the cross-sectional diameter of the passage 20 and correspondingly decrease the constrictive, collapsing, bending, folding or some other reconfiguring force or pressure applied by the device 10 to the exterior surface of the urethra 2.

As indicated above there are a number of possible ways that the constrictive, collapsing, bending, folding or some other reconfiguring force or pressure may be applied by the device 10 to the exterior surface of the urethra 2. Such constrictive, collapsing, bending, folding or some other reconfiguring force or pressure applied by the device 10 can result from the preformed or molded configuration of the device 10, the shape and/or type of medium that is encapsulated within the bio-compatible bladder and/or by the fact that the outer wall or surface 12 of the device is less pliable relative to that of the inner wall or surface 18 which is in contact with the urethra 2. The outer wall or surface 12 is typically made noncompliant or less pliable than the inner wall or surface 18 by, for example, altering the wall thickness, imparted material properties by means of any acceptable processes such as laminating the outer wall with other materials and/or forming the outer wall 12 with circumferential ribbing 29.

Figure 4:
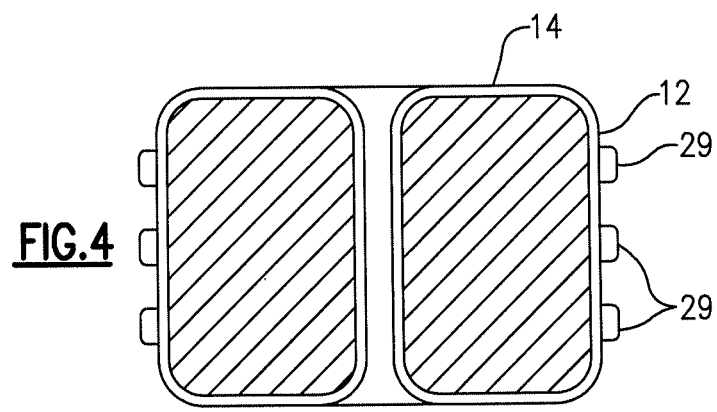
FIG. 4 is a diagrammatic cross sectional view of a further embodiment of the device according to the invention having a single shell.

As shown in FIG. 3, at least one layer 15 is laminated to the outer wall 12 to increase the thickness and reduce the pliancy or pliability of the outer wall 12 with respect to the inner wall or surface 18. In addition, the laminate layer 15 may also partially or completely extend over either, or both of, the inlet and the outlet end surfaces 14, 16 of the device 10. One or more ribs 29, as seen in FIG. 4, can wrap or extend completely around the outer wall 12 of the device 10 to further increase the rigidity and/or reduce the pliancy or pliability of the outer wall 12. With such a design, the outer wall 12 will be more resistant to changes in pressure or force within the device 10 which results in the fact that all such pressures or forces are generally directed inwardly toward the inner wall 18 which interacts with the urethra 2.

Figure 5A:
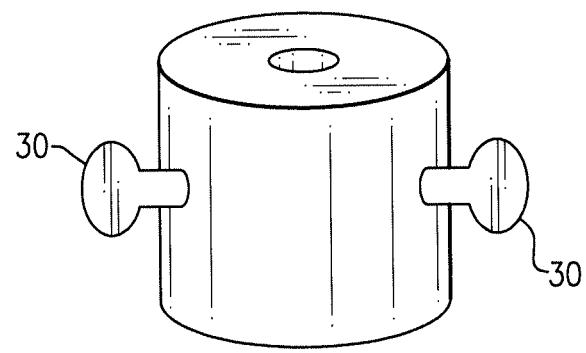
FIG. 5A is a diagrammatic perspective view of an embodiment of the device according to the invention having reservoirs.
Figure 5B:
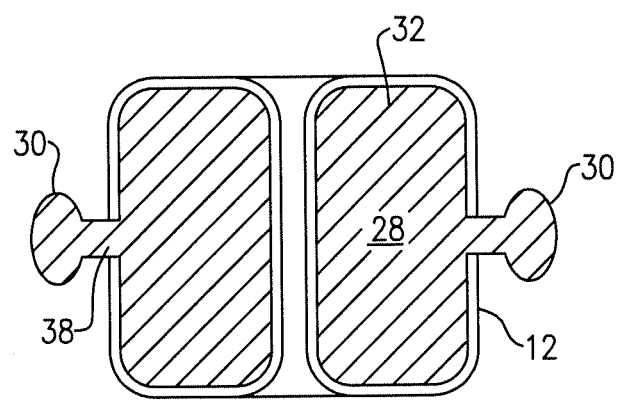
FIG. 5B is a diagrammatic cross sectional view of the embodiment of the device according to FIG. 5A.

As diagrammatically shown in FIGS. 5A and 5B, the device 19 may include two or more "ears", pouches or reservoirs 30 that are secured to and extend from the outer wall 12 of the device 10. The reservoirs 30 are more pliable than the outer wall 12 of the device 10 and may simply allow for the flow or transfer of the foam, gel, liquid, gas and/or other viscous medium 28, normally contained within an internal chamber 32 of the main body of the device 10, when the internal system pressure forces or biases the inner wall 18 (in contact with the urethra 2) normally radially outward thereby increasing the pressure or force within the internal chamber 32 of the main body. This increase in pressure or force within the internal chamber 32 is relieved by the flow of the displaced foam, gel, liquid, gas and/or other viscous medium 28 to one or both of the reservoirs 30. For this purpose alone, the reservoirs 30 would require little or possibly no pressure to inflate. The reservoirs 30 may simply receive the displaced foam, gel, liquid, gas and/or other viscous medium 28 and then normally return the displaced foam, gel, liquid, gas and/or other viscous medium 28 once the inner wall 18 of the device 10 returns back to its normal state as the internal system pressure in the urinary tract, from the micturition process, gradually diminishes. The reservoirs 30 may also serve as a pressure or force control for the device 10 by forcing the medium 28 back into the device 10 in the event that the reservoir(s) 30 stretches when receiving the displaced foam, gel, liquid, gas and/or other viscous medium 28. This is opposed to the reservoir 30 simply taking up the medium.

Figure 6A:
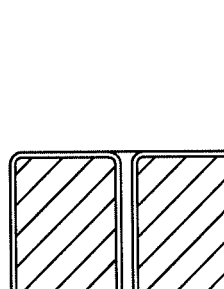
FIGS. 6A, 6B, 6C are diagrammatic cross sectional views of an embodiment of the device having different pressure controls and/or attachment means.

As shown in FIG. 6A, one or more remote reservoirs 34 may be connected or otherwise coupled to the interior chamber of the device 10 via a tube 36, with the remote reservoirs 34 being located at a distance from the device 10, instead of being fixed to and supported by the outer wall 12, as with the embodiment shown in FIGS. 5A and 5B. In either case, the opening 38 or the tube 36, coupled between the internal chamber of the main body 32 and the reservoir 30 or 34, may be used to control the flow of the medium within the sac, pouch or shell 26 thus providing a method of gradually releasing and applying an external pressure or force within the sac, pouch or shell 26 on the inner wall 18 of the device 10 and the urethra 2.

Figure 6B:
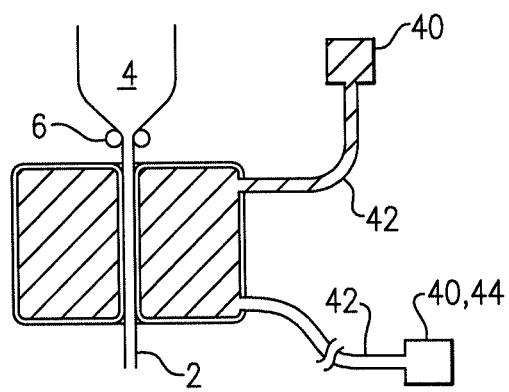

In a further embodiment shown in FIG. 6B, a manual pressure or force control device 40 can be coupled to the device 10, via a conduit 42, to facilitate manually controlling the pressure or force within the sac, pouch or shell 26 on the inner wall 18 and the urethra 2. The manual pressure or force control device 40 may be located spaced from the outer wall 12 of the device 10, adjacent to the sac, pouch or shell 26, at any physiologically sufficient location within the body cavity of the patient, or even possibly external to the body cavity, or possibly within the scrotum.

An external pressure control 44 (EPC) can be attached to the device 10, via a conduit 42, to mechanically control the pressure within the sac, pouch or shell 26 and thereby the obstruction pressure or force exerted on and/or by the inner wall 18 against the outer surface of the urethra 2. The external pressure control 44 may be mechanically manipulated such that actuation, in a first direction, increases the internal pressure within the sac, pouch or shell 26 while actuation in a second opposite direction reduces the internal pressure within the sac, pouch or shell 26. The external pressure control 44 can be located remote from the device 10, either in the scrotum or possibly external of the body cavity.

The sac, pouch or shell 26 of the device 10 may also be made of a self sealing material which accepts a hypodermic needle and suitably self seals itself once the hypodermic needle is removed from the device 10. Such a sac, pouch or shell 26 would facilitate adjustment of the pressure or force within the sac, pouch or shell 26 and thus the pressure or force exerted by the inner wall 18 against the outer surface of the urethra 2. In this manner, the volume of foam, gel, liquid, gas and/or other viscous medium 28, and thus the pressure or force within the internal chamber, could be readily adjusted at any time, even once the device 10 has been surgically implanted within the patient.

Further, the sac, pouch or shell 26 of the device 10 may be impregnated with an applicable pharmaceutical material(s) so as to be drug-eluting for (but not limited to) the purpose of preventing infection or stone build up at the surgical site or anastomosis and maybe radiopaque for radiological evaluation.

Figure 6C:
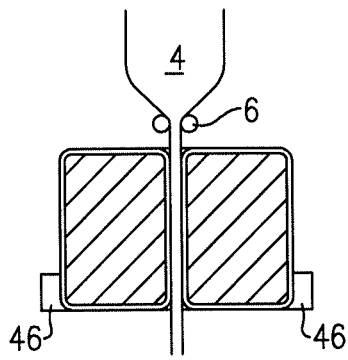

The device 10 may also contain external features to facilitate locating and securing of the device via the surgical procedure. External tabs or other features 46 that are designed to accept sutures, staples or any other conventional and accepted surgical apparatus may be used to simply hold the device 10 in place on and/or around the urethra 2 (see FIG. 6C, for example). The device 10 may also be held in a sling like fashion in such a position that the device 10 applies a generally vertically upward force on the bladder 4 for supporting the bladder 4. Alternatively, a band, a wrap or a belt may be used to increase the obstruction pressure or force that the device 10, e.g., the inner wall 18, transfers or imparts on the urethra 2 and such band, wrap or belt may be secured in place by means of one or more sutures and tabs 46.

Figure 7:
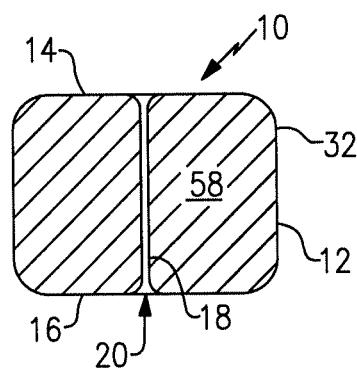
FIG. 7 is a diagrammatic cross sectional view of another embodiment of the device according to the invention formed without a shell.

As generally shown in FIG. 7, the device 10 may be manufactured from a foam, a gel or some other viscous material 58. This embodiment of the device 10 differs from the previous embodiments in that this device 10 does not comprise a sac, pouch or shell 26. That is, the foam, gel or other viscous material 58 is preformed, molded, cut or otherwise processed to have a specific shape, size and/or configuration. The foam, gel or other viscous material 58 is selected such that the device 10 is inherently compliant or pliable while, at the same time, the device 10 is sufficiently resilient. These characteristics allow the device 10 to retain the desired shape, size and/or configuration as well as normally induce the desired flow obstruction in the urethra 2, due to the shape, diameter or contour of the inner surface 18, while, at the same time, the device 10 is partially deformable so as to permit the desired flow of the urine through the urethra 2.

According to this embodiment, the device 10 comprises a preformed body 32 made of the foam, gel or other viscous material 58. In this embodiment, the device 10 comprises a circumferential outer surface 12 and inlet and outlet end surfaces 14, 16. The device 10 also has a radially inner surface 18 which defines a passage 20 that extends through the device 10 between the inlet and the outlet surfaces 14, 16. This embodiment of the device 10 generally functions in the same manner as described above. The foam, gel or other viscous material 58 that forms the device 10, in this case, is one or more bio-compatible materials.

As noted above, the preformed body 32 of the device 10 has a specific predetermined shape or form which is chosen to support any desired body part and also provide the desired flow obstruction in the urethra 2. In one embodiment, the device 10 is a single piece which has been formed into a generally "doughnut" shaped configuration. The device 10 has a central passage 10 that extends vertically completely through device 10 and the urethra 2 must be threaded through device 10 during the implantation procedure, e.g., the urethra is first cut and then reconnected to itself or possibly reconnected to a base of the bladder 4.

It is to be appreciated that the passage 20 may have a variety of different arrangements and configurations which all provide suitable flow obstruction of the urethra 2 so as to prevent the flow of fluid therethrough. For example, the inner wall or surface 18 of the device 10 that defines the passage 20 may be configured so as to be smooth, fluted, ribbed, spiral or knobby. In addition, the shape, diameter and/or contour of the wall or surface 18 may vary as long as the passage 20 induces the desired flow obstruction in the urethra 2, e.g., provides the proper pressure/flow relationship. The passage 20 may be straight, non-linear, curved, hour glass shaped or conical in either direction. It should be appreciated that the passage 20 is not limited to the specific configurations described herein.

Figure 8:
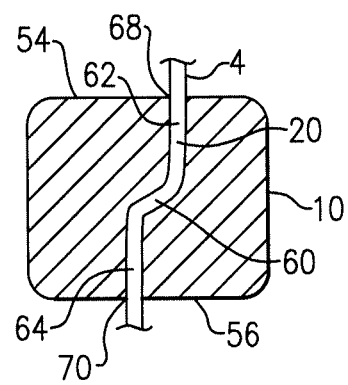
FIG. 8 is a diagrammatic cross sectional view of the device according to FIG. 7 formed without a shell and having a different passage configuration.
Figure 9:
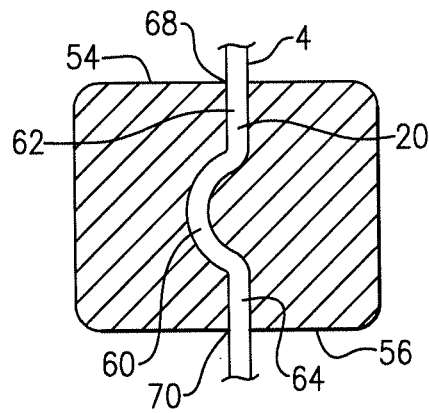
FIG. 9 is a diagrammatic cross sectional view of the device according to FIG. 7 formed without a shell and having another distinctive passage configuration.

A couple examples of the device 10 having a non-linear passage 20 for creating or inducing the desired flow obstruction are generally shown in FIGS. 8 and 9. The devices 10, as illustrated in those figures, comprise a generally centrally located passage 20 which extends vertically from an inlet end surface 54 of the device 10 to an outlet end surface 56 of the device 10. At one location between the inlet end surface 54 and the outlet end surface 56 of the device 10, the passage 20 includes a deviation 60 which causes, induces or creates the flow obstruction. As used herein the term deviation relates to a change in the axial path or course of the passage 20 as the passage extends through the device 10 from the inlet end surface 54 to the outlet end surface 56. The respective deviation 60, in each of these devices 10, is generally located centrally between the inlet end surface 54 and the outlet end surface 56 of the device 10, however, it is to be appreciated that the deviation 60 could be located any where between the inlet end surface 54 and the outlet end surface 56 of the device 10 and possibly two or more deviations 60 may be provided along the passage 20.

The deviation 60 in the device 10, shown in FIG. 8, is such that the axial path of an upper portion 62 of the passage 20 is offset from an axial path of the lower portion 64 of the passage 20, e.g., two bends or turns are provided therein. In such case, the passage inlet 68 in the inlet end surface 54 of the device 10 is vertically offset from a passage outlet 70 in the outlet end surface 56 of the device 10.

The deviation 60 shown in FIG. 9 is such that the path of the upper portion 62 of the passage 20 is axially aligned with the path of the lower portion 64 of the passage 20. As such, the passage inlet 68 in the inlet end surface 54 of the device 10 is also axially aligned with the passage outlet 70 in the outlet end surface 56 of the device 10. The deviation 60, which causes, induces or creates the flow obstruction in this embodiment of the device 10, is a "jut." That is, the passage 20 juts horizontally to one side before jutting horizontally back in such a manner that the upper and lower portions 62, 64 and the passage inlet and outlet 68, 70 of the passage 20 are substantially axially aligned with one another.

The physical characteristics of the foam, gel, liquid, gas and/or other viscous medium or material 58, used in the embodiments shown in FIGS. 7-9, are such that the medium or material 58 will allow for the device 10 to be pliable, so as to permit the desired flow through the urethra 2, and, at the same time, sufficiently resilient so as to return back to its initial shape and provide the desired flow obstruction in the urethra 2. With these characteristics, the device 10, or more specifically the shape of the device 10, will be able to conform to forces e.g. internal system pressures placed thereon and when these forces are discontinued or removed, the device 10 will normally return back to its originally manufactured shape. In this manner, changes in system pressure gradients and the flow of fluid through the passage 20 will cause the desired changes in the shape of the device 10 or more specifically the diameter of the passage 20 of the device 10. Furthermore, the device 10 will have the ability to maintain a specific design shape over an extended period of time as required.

Figure 10:
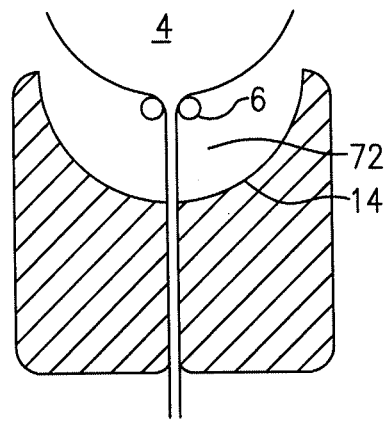
FIG. 10 is a diagrammatic cross sectional view of the device according to FIG. 7 having a void for supporting the bladder of a patient.

As shown in FIG. 10, in order to address the issue of excessive trauma to the anastomosis by the device 10 itself, the inlet end surface 14 of the device 10 may be configured to include a cavity 72 where the device 10 would generally contact the affected area of the body of the patient, e.g., a base of the bladder 4. As shown, the cavity 72 is a cup shaped surface or depression formed in the inlet end surface 54 of the device 10 that provides little or no contact with the anastomosis while still providing some support for the bladder 4 and enhancing placement of the device 10 within the patient.

Figure 11:
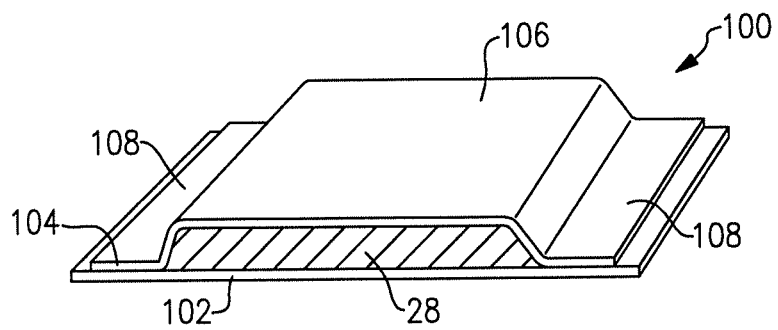
FIG. 11 is a diagrammatic cross sectional pictorial view of a further embodiment of the device according to the invention having a planar configuration.

Another embodiment of the device 100, as shown in FIG. 11, comprises a generally planar base layer 102 and top layer 104 that is bonded to the base layer 102 in such a manner that a shell or pocket 106 is formed between the base and top layers 102, 104 and the shell or pocket 106 extends axially along the length of the device 100. Similar to the embodiment described above, the shell or pocket 106 is filled with foam, gel, liquid, gas and/or some other viscous medium 28. In this embodiment, the shell or pocket 106 is generally a planar elevation, ridge or strip that extends along the length of the device 100. The outer side edges 108 of the device 100, i.e., the sides of the device 100 that are opposite one another, extend lengthwise of the device 10 and do not include the shell or pocket 106. That is, the outer side edges 108 of the device 100 only comprise the top and base layers 102, 104 and not the shell or pocket 106 or any of the foam, gel, liquid, gas or some other viscous medium 28.

Both the base and the top layers 102, 104 of the device 100 are sufficiently compliant and pliable with the top layer 104 being more compliant in comparison to the base layer 102. The greater compliancy of the top layer 104 enables the top layer 104 to move relative to the base layer 102 depending on the internal system pressures applied thereon. In the manner described above, the top layer 104 will generally be biased away from the base layer 102, when the pressure within the shell or pocket 106 increases and conversely, but toward the base layer 102, when the pressure within the shell or pocket 106 decreases or when the internal system pressure is acting on the shell or pocket 106. The differences in compliancy, between the base and the top layers 102, 104, can be achieved by a difference in the thickness of the two layers with the base layer 102 being thicker than the top layer 104. The differences in the types and/or kinds of materials which form the base and the top layers 102, 104 can also cause differences in the compliancy of the two layers. In this manner, the top layer 104 is formed by a material that is more compliant than the material which forms the base layer 102.

Figure 12:
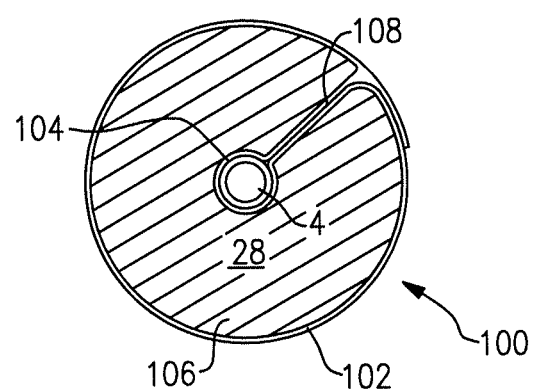
FIG. 12 is a diagrammatic cross sectional view of the device according to FIG. 11 wrapped around the urethra of a patient.

When this embodiment of the device 100 is implanted in a patient, the device 100 is wrapped around the urethra 2 and the two opposed outer ends 108 are bonded or otherwise permanently connected together via an adhesive, ultrasonic welding or any other surgically acceptable or conventional means (FIG. 12). In this case, the device 100 is in the general form of a sleeve which surrounds and normally applies a desired radially directed pressure or force on the exterior surface of the urethra 2 which is suitable to temporarily obstruct the flow of urine through the urethra 2. It is to be appreciated that the two opposed side edges 108 of the device 100 could be bonded with one another, before the device 100 is surgically implanted, but this method of implanting the device 100 would require the urethra 2 to be severed and then reconnected, which is typically less desirable. As with the previously described devices, the urethra 2 would extend axially through the device 100 and provide the desired flow obstruction and flow passage for the urethra 2, as described above.

As shown in FIG. 12B, the device 100 may be utilized in the generally planar configuration shown in FIG. 11. In this planar configuration, the device 100 is implanted such that the urethra 2 is located between the top layer 104 of the shell or pocket 106 of the device 100 and some other anatomical structure 110, e.g., a pelvic bone, muscle, etc., so as to provide the desired flow obstruction in the urethra 2 by collapsing, constricting, sandwiching or otherwise crimping the urethra 2, between the shell or pocket 106 of the device 100 and the anatomical structure 110 as well as allow the desired flow passage upon suitable deformation of the top layer 104 of the device 100 and thereby continue to allow for normal function of the urinary tract.

FIGS. 12 and 12A show a modified version of the device 100 in which the device 100 generally has a cut or slit 107 that extends from an outer wall radially inwardly toward the passage 20 and along the entire length of the device 100. According to this embodiment, during the surgical procedure, the slit 107 is separated so as to facilitate placing the device 100 around the urethra 2 whereby thereafter the urethra 2 is completely accommodated within the passage 20. This embodiment avoids having to cut or otherwise sever the urethra 2. As with the previous embodiments, one or more rib(s) or other circumferential element(s) can wrap or extend completely around the outer wall or surface of the device 100 to maintain the slit 107 in the substantially closed position.

In a similar embodiment, as shown in FIG. 13, the device 100 may comprise two or more shells or pockets 106 each filled with the selected foam, gel, liquid, gas and/or other viscous material or medium 28. This embodiment of the device 100 is similar to the preceding embodiment in that the device 100 comprises a generally planar a base layer 102 and a top layer 104 that is bonded to the base layer 102. However, according to this embodiment the top and the base layers 104, 102 are bonded to one another at three different locations along the width of the device 100 so as to form two or more separate shells or pockets 106, e.g., generally planar elevations, ridges or strips that extend axially along the length of the device 100. Each shell or pocket 106 is each filled with a foam, gel, liquid, gas and/or some other viscous medium 28. By bonding or otherwise securing the top layer 104 to the bottom layer 102 at a number of locations along the width of the device 100, one or more troughs 112 are formed between the shells or pockets 106 and likewise extends along the length of the device 100.

As previously described above, the device 100 can be implanted by either wrapping the device 100 around the urethra 2 or connecting and the device 100 to another anatomical structure, as described above. When the device 100 is wrapped around the urethra 2, the outer side edges of the device 100 are bonded together via an adhesive, ultrasonic welding or any other surgically acceptable or conventional means. In this case, the device 100 is in the general form of a sleeve, as shown in FIG. 14, which surrounds and applies a suitable force or pressure to the exterior surface of the urethra 2 and thereby provides the desired flow obstruction which prevents urine from flowing along the urethra 2. The urethra 2 passes through the device 100 and is sandwiched or clamped between the two or more mating pairs of shells or pockets 106.

FIGS. 14A, 14B, 14C, 14D are diagrammatic cross sectional illustrations of the device 100 having two or more separate shells or pockets 106 that have been partially wrapped around the urethra 2 and sandwich or otherwise accommodate the urethra 2 therebetween. That is, each one of the two or more separate shells or pockets 106 combined with one another to generally form a cylindrical or sleeve like configuration which totally surrounds and encloses the urethra 2. As with the previous embodiments, one or more rib(s) or other circumferential element(s) can wrap or extend completely around the outer wall or surface of the device 100 to maintain the slit 107 in the substantially closed position.

Figure 14A:
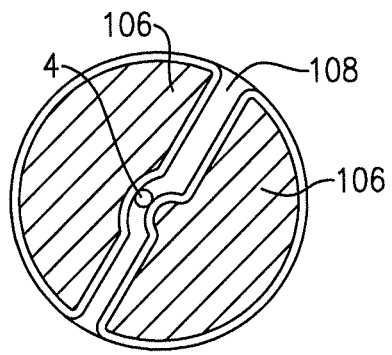
FIGS. 14A, 14B, 14C, 14D are diagrammatic cross sectional views of the device, according to FIG. 13, wrapped around the urethra of a patient and having various shell configurations.
Figure 14B:
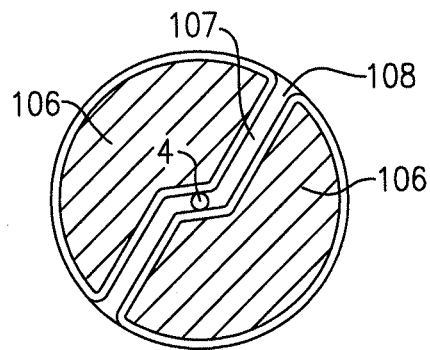
Figure 14C:
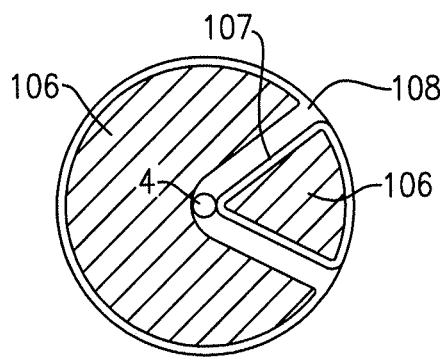
Figure 14D:
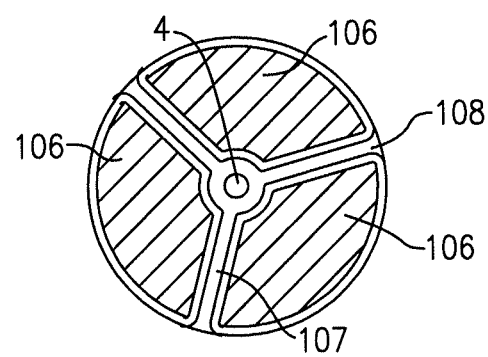

The top layer 104 of the shells or pockets 106 can be formed having specific features so as to provide the device 100 with different cross sectional configurations, for example. The shells or pockets 106 and device 100 can have a simple clam shell configuration, with or without a passage, as shown in FIG. 14. A passage and tab (or notch and key) configuration is shown in FIG. 14A. The shells or pockets 106 and the device 100 can be configured to include a passage formed by mating sides, as shown in FIG. 14B, or a V-shaped passage, as shown in FIG. 14C. FIG. 14D shows a configuration with multiple chambers.

Figure 15A:
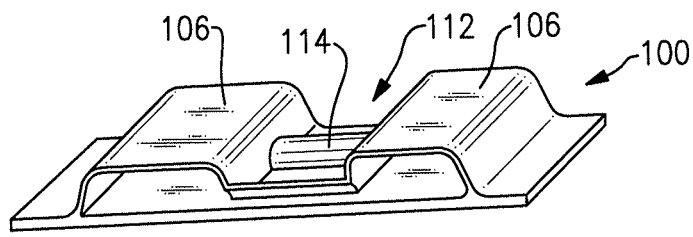
FIG. 15A is a diagrammatic cross sectional perspective view of the device, according to FIG. 13, with a conduit extending between the two shells.
Figure 15B:
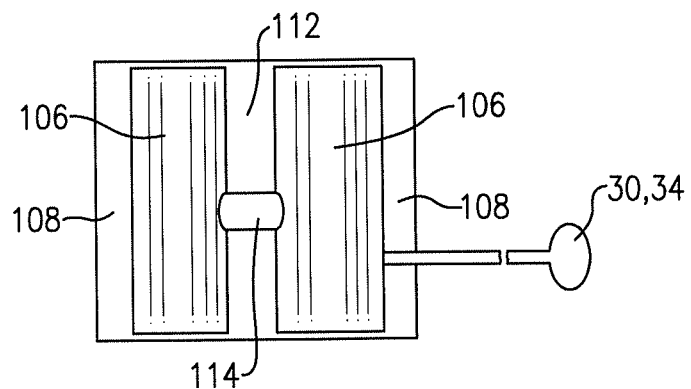
FIG. 15B is a diagrammatic top plan view of the device, according to FIG. 13, with a conduit extending between the two shells and having a reservoir for adjusting the pressure of the shells.

It is possible in the embodiments of the device 100 formed with two or more shells or pockets 106 that the shells or pockets 106 can be either independent of another or one or more of the individual chambers 106 may be connected with one another by a conduit 114 such that the foam, gel, liquid, gas and/or some other viscous medium 28 can readily pass and flow therebetween, as diagrammatically shown in FIGS. 15A and 15B. Further, these embodiments of the device 100 can also comprise "ears," pouches or reservoirs 34 which function, as previously described above.

Figure 16B:
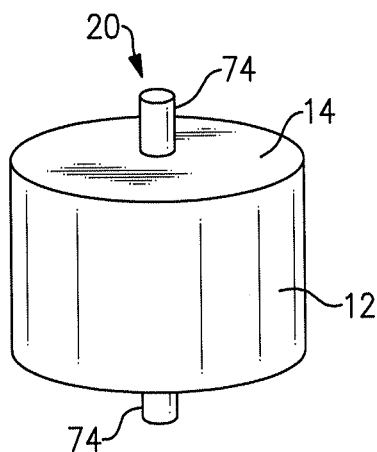
FIG. 16B is a diagrammatic perspective view of the device according to FIG. 16A.
Figure 16A:
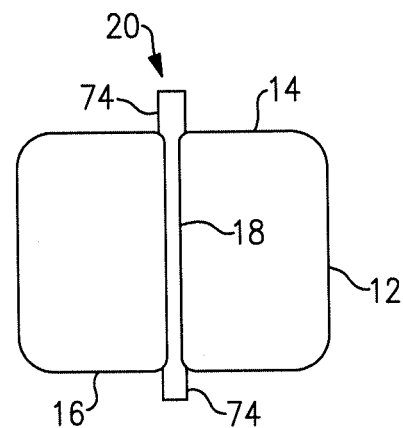
FIG. 16A is a diagrammatic cross sectional view of an embodiment of the device with an inlet and an outlet neck for anastomosing the urethra to the device.

FIGS. 16A and 16B illustrate another embodiment of the device 10 which includes a protruding inlet and/or outlet neck or collar 74. During surgical implantation of the device 10, the neck or collar 74 facilitates anastomosizing of the urethra 2 to the device 10. In one example of this embodiment, the neck or collar 74 is formed by an extension of the inner wall 18 of the device 10. As seen in FIG. 16A, the inner wall 18 of the device 10 extends a desired distance from both the inlet and the outlet end surfaces 14, 16 of the device 10. The neck or collar 74 of the device 10 can be modified, i.e., either shortened or lengthened, depending on the specific requirements of the patient. Implantation of this form of the device 10 requires that the urethra 2 be cut or severed. Once the device 10 has been located within the patient the severed ends of the urethra 2 are sutured or otherwise connected to the necks or collars 74 of the device 10 in a known manner.

It should be recognized that although the device has been described herein as a device for treating urinary incontinence, the device could be resized and reconfigured to treat or augment the function of other anatomical or physiological abnormalities or anomalies which compromise the pressure and/or a flow and which require corrective measures to ensure proper anatomical or physiological function to an organ, system or body. The device may be used to correct or treat deficiencies and/or insufficiencies such as: esophageal/gastric herniation or gastroesophageal reflux disease (GERD). The device may be configured as a laparoscopic adjustable gastric band (Lap Band) type of device for the treatment and/or correction of obesity in bariatric patients. Further, the device could be configured to treat or support arterial or venous aneurysms. Still further, the device may be configured to treat and/or repair anatomical eventrations such as herniation of the intestines. The device could be configured to replace or augment organs or tissues which function to transfer air, fluids or solids by controlling and regulating pressure and/or flow, e.g., colon, rectum, sphincters, etc. Any time an anatomical sphincter requires support in form and/or function and/or needs replacement, the device can be configured to correct, augment and/or treat a variety of herniations and vericosities.

Since certain changes may be made in the above described device for the treatment of urinary incontinence, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, we claim:

1. A device for treating urinary incontinence, the device comprising:

a body comprising a preshaped foam or gel encapsulated within an outer shell, and the device only defining a single interior chamber therein, the device being fluid tight and having an uninterrupted outer surface and all of the foam or gel being contained within the single interior chamber, the body having an inner surface defining a through passage, for communicating with a urethra of a patient, and the passage extending from an inlet to an outlet of the device and the inner surface being biased, by the foam or gel, radially inwardly into a flow obstruction position, the passage being configured so that, following surgical implantation of the device in the patient, a section of the urethra communicates with the passage of the device, and the foam or gel normally automatically and continuously exerts an obstruction force on the inner surface, without any external control or actuation of a pump, which collapses the inner surface radially inward so as to form a flow obstruction which obstructs flow of fluid along the urethra;

the inner surface of the device being sufficiently pliable and deformable so that only when an internal system pressure, of a fluid flowing within and through the urethra, becomes greater than the obstruction force applied by the foam or gel against the inner surface, the flow obstruction, induced by the inner surface, is overcome and the greater internal system pressure of the fluid within the urethra compresses the foam or gel and biases the inner surface of the passage radially outward, due to the greater internal system pressure within the urethra which is exerted on the inner surface, and the urethra automatically and gradually achieves a urethra patent state which permits fluid flow through the urethra; and once the internal system pressure of the fluid within the urethra becomes less than the obstruction force applied by the foam or gel against the inner surface, the inner surface is automatically biased radially inward, due to the greater pressure applied by the foam or gel, so that the urethra automatically and gradually achieves a urethra non-patent state which blocks flow of fluid through the urethra so that the flow of fluid along the urethra is controlled solely by a change of the internal system pressure in the passage.

2. The device for treating urinary incontinence according to claim 1, wherein the passage is located within the body and the passage is defined by the inner surface which has a greater elasticity than an elasticity of an outer surface of the device such that deformation of the inner surface is solely dependent on an increase of the internal system pressure within the urethra.

3. The device for treating urinary incontinence according to claim 2, wherein the passage extends from an inlet end to an outlet end of the device.

4. The device for treating urinary incontinence according to claim 3, wherein the inner surface is thinner than at least an outer wall of the device.

5. The device for treating urinary incontinence according to claim 3, wherein the body of the device includes at least one cut out, slit or other opening in a side wall of the device which facilitates wrapping the device around the urethra without having to sever the urethra.

6. The device for treating urinary incontinence according to claim 3, wherein the passage of the device extends axially through the device from the inlet end to the outlet end.

7. The device for treating urinary incontinence according to claim 3, wherein the inner surface of the device is formed such that the passage comprises at least one passage deviation located between the inlet end and the outlet end.

8. The device for treating urinary incontinence according to claim 3, wherein the inner surface includes first and second necks, the first neck projects from an inlet end surface and the second neck extends from an outlet end surface, each of the first and the second necks are connectable with a respective severed end of the urethra.

9. The device for treating urinary incontinence according to claim 2, wherein the body comprises inlet and outlet end surfaces, the inner surface has a greater elasticity relative to an elasticity of the outer surface and an inner portion of the inlet and the outlet end surfaces, adjacent the inner surface, has a greater elasticity relative to an elasticity of an outer portion of the inlet and the outlet surfaces adjacent the outer surface.

10. The device for treating urinary incontinence according to claim 9, wherein the inlet end surface of the device comprises a voided area such that the device has a cup shaped cross section.

11. The device for treating urinary incontinence according to claim 2, wherein the inner surface is a surface of an inner wall of the device and the outer surface is a surface of an outer wall of the device and the inner wall is thinner than the outer wall and has a greater elasticity in comparison to an elasticity of the outer surface.

12. The device for treating urinary incontinence according to claim 2, wherein at least one rib surrounds and circumscribes the outer surface of the device so as to minimize radially outward movement of the outer surface with respect to the inner surface and promote radially outward movement by the inner surface.

13. The device for treating urinary incontinence according to claim 2, wherein the outer surface of the device comprises at least one tab which facilitates securing the device to a body of the patient.

14. A device for treating urinary incontinence consisting of:
  a fluid tight shell encasing a body and the shell device having an uninterrupted outer surface,
  the body having a laterally outer surface, a top surface, a bottom surface and an inner surface, which defines a passage that extends at least through the device from an inlet end to the bottom surface;
  the top surface and the bottom surface being integral with axially opposite ends of each of the inner surface and the outer surface to define only a single interior chamber within the device;
  the interior chamber of the device being completely filled with a foam or gel which is pliable and sufficiently resilient; and
  the inner surface being movable with respect to the outer surface between a first position and a second position depending solely on a difference between a pressure difference applied radially inward by the foam or gel against the inner surface and a system pressure of a fluid contained within a urethra such that a diameter of the passage, when the inner surface is in the first position, is smaller than a diameter of the passage when the inner surface is in the second position; and
  when the pressure applied radially inward by the foam or gel against the inner surface is overcome by a greater pressure exerted by the fluid contained within the urethra, the foam or gel is gradually compressed and deformed and the inner surface is biased radially outward, solely due to the greater pressure of the fluid within the urethra, so that the inner surface is moved toward the second position in which flow of the fluid along the urethra is permitted.

15. The device for treating urinary incontinence according to claim 14, wherein the foam or gel is preformed to a desired shape, the preformed foam or gel is encasable by the shell, and the diameter of the passage is automatically changed solely by a change of the system pressure in the passage.

16. The device for treating urinary incontinence according to claim 14, wherein the inner surface is in the first position when the pressure applied radially inward by the inner surface is greater than the system pressure in the passage and the inner surface is in the second position when a constrictive force applied radially inward by the inner surface is less than the system pressure in the passage.

17. A device for treating urinary incontinence comprising:
  a shell comprising a laterally outer wall, a top wall, a bottom wall and an inner wall, which defines a passage that extends at least through the device from the top wall to the bottom wall;
  the top wall and the bottom wall being respectively integral with axially opposite ends of each of the inner wall and the outer wall to define an interior of the device;
  the interior of the device being substantially entirely filled with a preformed foam such that a constrictive force is applied on tile inner wall by the foam from within the interior of the device; and
  the inner wall being movable with respect to the outer wall between a first relaxed position and a second open position depending solely on a difference between the constrictive force applied on the inner wall by the foam from within the interior of the device and a system pressure applied on the inner wall by the urethra such that a diameter of the passage, when the inner wall is in the first relaxed position, is smaller than a diameter of the passage when the inner wall is in the open position;
  wherein when the constrictive force, applied radially inward by the inner surface, is overcome by a force exerted on the inner surface of the passage due to a greater system pressure of fluid contained within the urethra, the inner surface deforms outwardly into the second open position, due to the greater system pressure of the fluid within the urethra, and the urethra achieves a urethra patent state which permits flow through the urethra; and
  wherein once the system pressure of the fluid in the urethra becomes less than the constrictive force, applied radially inward by the inner surface, the inner surface moves inwardly, due to greater pressure exerted by the device, into the first relaxed position and the urethra again achieves a non-patent state which prevents flow through the urethra.

* * * * *